(12) United States Patent
Kitano et al.

(10) Patent No.: US 8,704,188 B2
(45) Date of Patent: Apr. 22, 2014

(54) PORTABLE RADIOGRAPHIC IMAGE CAPTURE DEVICE, IMAGE CAPTURE CONTROLLER, AND RADIOGRAPHIC IMAGE CAPTURE SYSTEM

(75) Inventors: Kouichi Kitano, Kanagawa (JP); Kentaro Noma, Kanagawa (JP); Yukihisa Ikegame, Kanagawa (JP)

(73) Assignee: Fujifilm Corporation, Tokyo (JP)

( * ) Notice: Subject to any disclaimer, the term of this patent is extended or adjusted under 35 U.S.C. 154(b) by 214 days.

(21) Appl. No.: 13/305,477

(22) Filed: Nov. 28, 2011

(65) Prior Publication Data

US 2012/0163542 A1 Jun. 28, 2012

(30) Foreign Application Priority Data

Dec. 28, 2010 (JP) ................................. 2010-292140

(51) Int. Cl.
*G01T 1/24* (2006.01)
(52) U.S. Cl.
USPC ..................................................... 250/370.09
(58) Field of Classification Search
USPC ............. 250/370.09; 378/98.8, 116, 162, 165
See application file for complete search history.

(56) References Cited

U.S. PATENT DOCUMENTS

2007/0140424 A1   6/2007   Serceki

FOREIGN PATENT DOCUMENTS

| JP | 2005-006979 A | 1/2005 |
| JP | 2007-167649 A | 7/2007 |

*Primary Examiner* — David Porta
*Assistant Examiner* — Hugh H Maupin
(74) *Attorney, Agent, or Firm* — Jean C. Edwards; Edwards Neils PLLC

(57) ABSTRACT

A portable radiographic image capture device includes a radiographic image data generating unit, a wired communication unit that and performs wired communication with an image capture controller; a wireless communication unit that performs wireless communication with a communication base station; a storing unit that stores first wireless communication configuration data related to a first communication base station; and an update unit that, when the image capture controller is wire-connected, acquires from the image capture controller second wireless communication configuration data related to a second communication base station with which the image capture controller performs wireless communication, and updates the first wireless communication configuration data with the acquired second wireless communication configuration data.

9 Claims, 9 Drawing Sheets

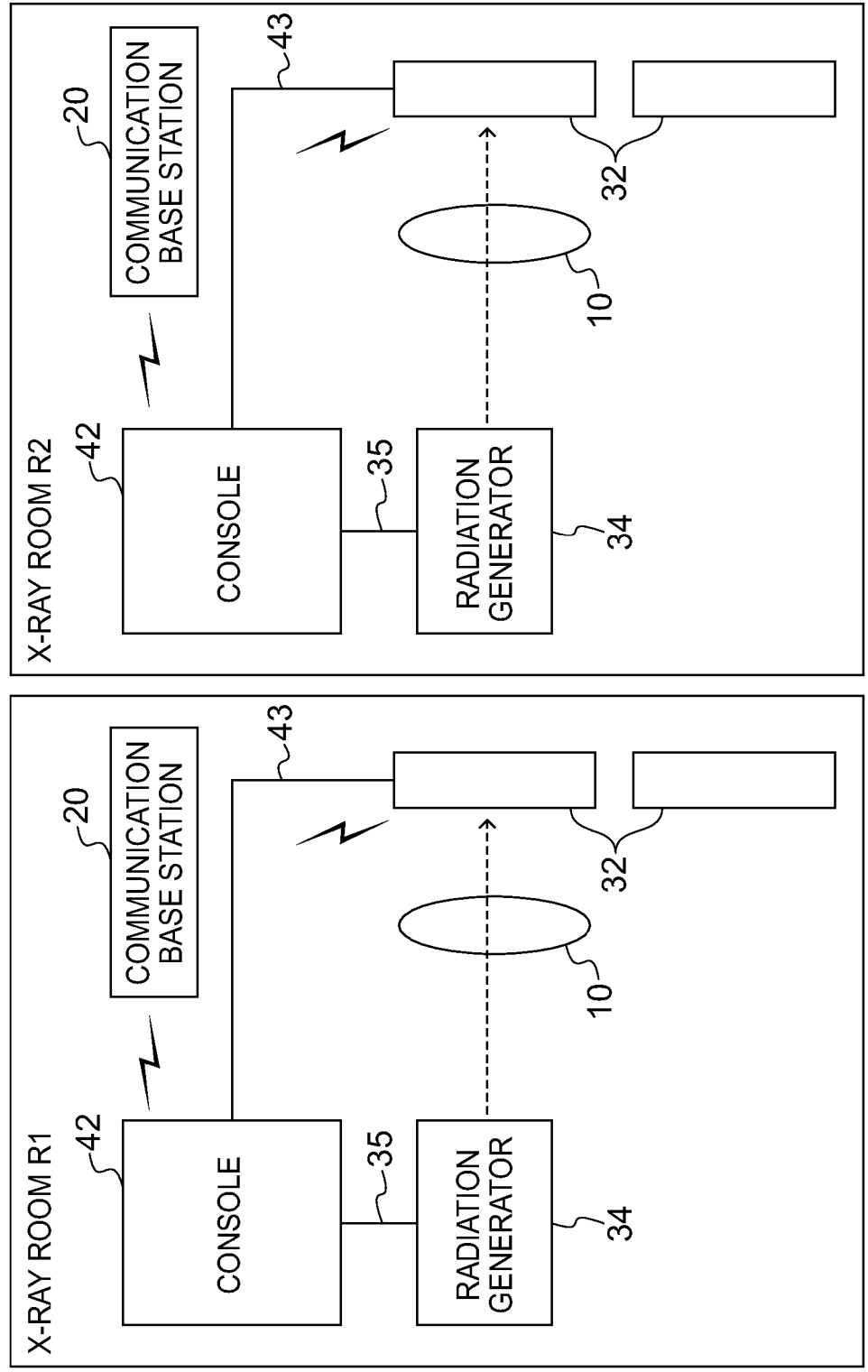

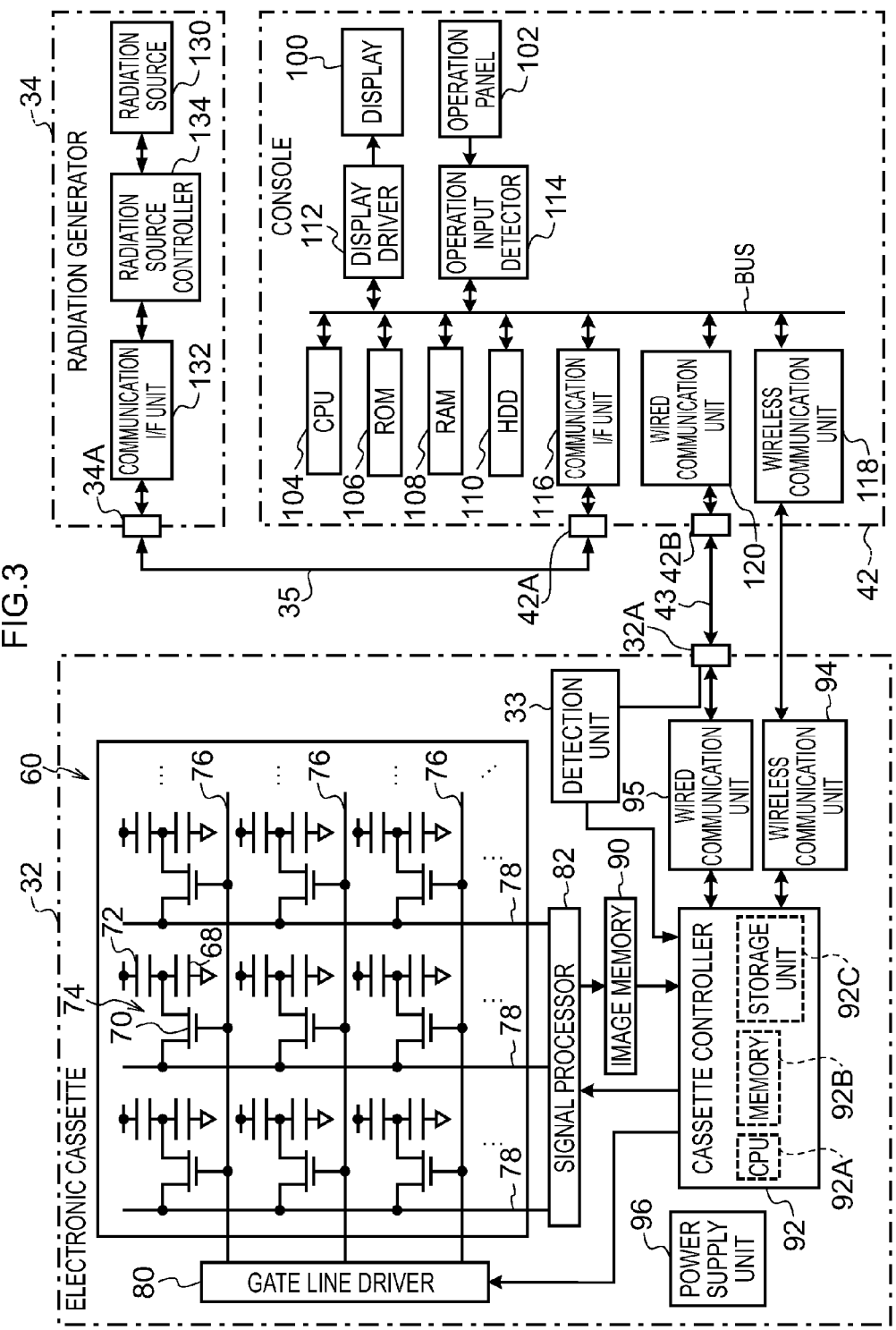

PORTABLE RADIOGRAPHIC IMAGE CAPTURE DEVICE, IMAGE CAPTURE CONTROLLER, AND RADIOGRAPHIC IMAGE CAPTURE SYSTEM

CROSS-REFERENCE TO RELATED APPLICATION

This application claims priority under 35 USC 119 from Japanese Patent Application No. 2010-292140 filed on Dec. 28, 2011, the disclosure of which is incorporated by reference herein.

BACKGROUND OF THE INVENTION

1. Field of the Invention

The present invention relates to a portable radiographic image capture device, an image capture controller, and a radiographic image capture system that can perform wireless communication and wired communication.

2. Description of the Related Art

In recent years, a radiation detector such as a flat panel detector (FPD) has been put into practical use in which a radiation-sensitive layer is disposed on a thin film transistor (TFT) active matrix substrate and which thus can directly convert radiation into digital data. A portable radiographic image capture device (hereinafter, also referred to as an "electronic cassette") has been put into practical use which generates by the FPD image information (data) indicating a radiographic image representing applied radiation and which stores the generated image data.

Examples of the electronic cassette include not only an electronic cassette that can perform wired communication by connecting via a cable to an image capture controller (so-called a console), which controls capture of a radiographic image, but also an electronic cassette that can perform wireless communication. Japanese Patent Application Laid-Open (JP-A) No. 2005-6979 discloses a technology of such a electronic cassette that can perform both wired and wireless communication, in which the communication mode is switched by connection and disconnection of a cable.

According to the technology disclosed in JP-A No. 2005-6979, in a case in which a cable is connected to a body of the electronic cassette, a wired communication is initiated. In a case in which the cable is not connected to the body of the electronic cassette, a wireless communication is initiated. However, a hospital may have many radiographic image capture rooms, and each image capture room may be equipped with many electronic cassettes. Further, since the electronic cassettes are portable, the electronic cassettes may be carried to various radiographic image capture rooms and used in any of the rooms.

Under this situation, in a case in which one communication base station is provided for each of radiographic image capture rooms where the radiographic image capture system is disposed and a wireless communication is performed based on a wireless communication configuration such as an extended service set identifier (ESSID) or a channel which is uniquely set for each of the radiographic image capture rooms (each communication base station), following situation may occur. If the electronic cassette is not moved between the radiographic image capture rooms, a radiographic image can be captured without causing any trouble, using the electronic cassette having the wireless communication configuration information (data) corresponding to each of the radiographic image capture rooms. However, if the electronic cassette (electronic cassette S) of a radiographic image capture room (image capture room A) is moved to another radiographic image capture room (image capture room B), and thereafter an operator (user) mistakenly selects the electronic cassette S that is does not exist in the image capture room A as an electronic cassette to be used for capture in the image capture room A, under a situation in which electric waves can be received in both of the image capture room A and the image capture room B, if the wireless communication configuration of the electronic cassette S is not changed, the electronic cassette S that has been moved to and thus existing in the image capture room B may be controlled through the wireless communication by the console of the image capture room A from which the electronic cassette S has been moved. This situation causes erroneous image capture and thus requires recapturing, which results in causing a subject to be unnecessarily exposed to the radiation. Meanwhile, in the image capture room B where the electronic cassette S is moved, the electronic cassette S cannot be selected as an electronic cassette that can be used for image capture.

Under a situation in which the electric waves cannot be received in the image capture room A and the image capture room B, the electronic cassette S that has been moved to the image capture room B cannot be selected and used in both the image capture room A and the image capture room B.

The technology disclosed in JP-A No. 2005-6979 does not considers the case in which the electronic cassette is moved between different image capture rooms and thus cannot resolve the above situation. Although a user may manually set the wireless communication configuration when an electronic cassette is moved to another radiographic image capture room, this is very troublesome and a setting error may occur at the time of the manual setting. For example, if wireless communication configuration data that is not used in any of the image capture rooms is set to an electronic cassette, communication with the electronic cassette cannot be performed in any of the image capture rooms. If an electronic cassette is set with wireless communication configuration data for a different image capture room from an image capture room to which the electronic cassette has been moved, the electronic cassette responds to an image capture request from the different image capture room and thus an image capture error may be occur in the different image capture room. In addition, the electronic cassette cannot be used for image capture in the image capture room to which the electronic cassette has been moved.

SUMMARY

The invention has been made in view of the above circumferences, and is to provide a portable radiographic image capture device, an image capture controller, and a radiographic image capture system that can automatically update wireless communication configuration information (data) held in the portable radiographic image capture device without a user intervening, prevent failure of capture of a radiographic image due to selecting a portable radiographic image capture device disposed in a different image capture room, and thereby prevent a patient (subject) from unnecessary exposure of radiation.

A first aspect of the present invention is a portable radiographic image capture device that includes: an image data generating unit that generates radiographic image data from irradiated radiation; a wired communication unit that includes a connecting terminal, and performs wired communication with an image capture controller that is wire-connected to the connecting terminal; a wireless communication unit that performs wireless communication with a communication base station; a storing unit that stores first wireless communication configuration data related to a first communication base station with which the wireless communication unit performs wireless communication; and an update unit that, when the image capture controller is wire-connected to the connecting terminal, acquires from the image capture controller second wireless communication configuration data related to a second communication base station with which the image capture controller performs wireless communication, and updates the first wireless communication configuration data held in the storing unit with the acquired second wireless communication configuration data.

According to the first aspect, since the second wireless communication setting data related to the second communication base station with which the image capture controller performs the wireless communication is acquired from the image capture controller and the first wireless communication setting data is updated, the wireless communication setting data that is held in the portable radiographic image capture device can be automatically updated without a user intervening. Further, the (first) communication base station with which the portable radiographic image capture device performs the wireless communication can be set as the same (second) communication base station as that of the image capture controller that is wire-connected. Therefore, in a case in which a communication base station performing the wireless communication is provided for each image capture controller (for each room in which the image capture controller is disposed), even if the combination of the radiographic image capture device and the image capture controller is changed (the portable radiographic image capture device is moved to and used in another room), the portable radiographic image capture device can update the (first) wireless communication configuration data by wire-connecting to the combined image capture controller, and can communicate with the (second) communication base station which the image capture controller communicates. For this reason, failure of radiographic image capture due to selecting a portable radiographic image capture device disposed in a different image capture room, and exposure of a subject to unnecessary radiation, can be prevented.

In the first aspect, the first and second wireless communication configuration data may include data that identifies a communication base station to be connected when wireless communication is performed.

A second aspect of the present invention is an image capture controller that includes a connecting terminal that is used to perform wired connection with a portable radiographic image capture device, which includes an image data generating unit that generates radiographic image data from irradiated radiation, a first wired communication unit that performs wired communication with the image capture controller when wire-connected thereto, a first wireless communication unit that performs wireless communication with a communication base station, a storing unit that stores first wireless communication configuration data related to a first communication base station with which the first wireless communication unit performs wireless communication, and an update unit that updates the wireless communication configuration data held in the holding unit; a second wired communication unit that performs wired communication with the portable radiographic image capture device wire-connected to the connecting terminal; a second wireless communication unit that performs wireless communication with a second communication base station; and a controlling unit that effects control such that, when the portable radiographic image capture device is wire-connected to the connecting terminal, second wireless communication configuration data related to the second communication base station is transmitted to the portable radiographic image capture device, and the update unit updates the first wireless communication configuration data stored in the storing unit with the second wireless communication configuration data.

A third aspect of the present invention is an image capture controller that includes: a connecting terminal that is used to perform wired connection with a portable radiographic image capture device; a wired communication unit that performs wired communication with the portable radiographic image capture device wire-connected to the connecting terminal; a wireless communication unit that performs wireless communication with a communication base station; and a controlling unit that performs a control such that, when the portable radiographic image capture device is wire-connected to the connecting terminal, wireless communication configuration data related to the communication base station is transmitted to the portable radiographic image capture device, and wireless communication configuration data stored in the portable radiographic image capture device is updated with the transmitted wireless communication configuration data.

According to the second and third aspects, since the (second) wireless communication setting data related to the second communication base station with which the image capture controller performs the wireless communication is transmitted to the portable radiographic image capture device that is wire-connected and the (first) wireless communication setting data of the portable radiographic image capture device is updated, the (first) wireless communication setting data that is stored in the portable radiographic image capture device can be automatically updated without a user intervening. Therefore, similarly to the first aspect, failure of radiographic image capture due to selecting a portable radiographic image capture device disposed in a different image capture room and an exposure of a subject to unnecessary radiation can be prevented.

In the second and third aspects, the wireless communication configuration data may include data that identifies a communication base station to be connected when wireless communication is performed.

A fourth aspect of the invention is a radiographic image capture system that includes: the portable radiographic image capture device according to the first aspect, wherein the update unit acquires the second wireless communication configuration data by making a request to an image capture controller; and an image capture controller that includes: a second wired communication unit that performs wired communication with the portable radiographic image capture device that is wire-connected thereto; a second wireless communication unit that performs wireless communication with the second communication base station; and a controlling unit that effects control such that, when the image capture controller is wire-connected to the connecting terminal of the portable radiographic image capture device and receives the request from the portable radiographic image capture device, the second wireless communication configuration data related to the second communication base station is transmitted to the portable radiographic image capture device.

Because the fourth aspect operates similarly to the first aspect, the (first) wireless communication setting data that is stored in the portable radiographic image capture device can be automatically updated without a user intervening, and failure of radiographic image capture due to selecting a portable radiographic image capture device disposed in a different image capture room and an exposure of a subject to unnecessary radiation can be prevented.

In the fourth aspect, the first and second wireless communication configuration data may include data that identifies a communication base station to be connected when wireless communication is performed.

A fifth aspect of the invention is a radiographic image capture system that includes: a portable radiographic image capture device including: an image data generating unit that generates radiographic image data from irradiated radiation; a first wired communication unit that performs wired communication with an image capture controller that is wire-connected; a first wireless communication unit that performs wireless communication with a first communication base station; a storing unit that stores first wireless communication configuration data related to the first communication base station; and an update unit that updates the first wireless communication configuration data stored in the storage unit; and the image capture controller according to the second aspect.

As such, the fifth aspect operates similarly to the second and third aspects, the (first) wireless communication setting data that is stored in the portable radiographic image capture device can be automatically updated without a user intervening, and failure of radiographic image capture due to selecting a portable radiographic image capture device disposed in a different image capture room and an exposure of a subject to unnecessary radiation can be prevented.

In the fifth aspect, the first and second wireless communication configuration data may include data that identifies a communication base station to be connected when wireless communication is performed.

According to the above aspects, the (first) wireless communication configuration data that is stored in the portable radiographic image capture device can be automatically updated without a user intervening.

BRIEF DESCRIPTION OF THE DRAWINGS

Exemplary embodiments of the present invention will be described in detail based on the following figures, wherein:

FIG. 1 is a block diagram illustrating the configuration of a radiographic image capture system according to first and second exemplary embodiments;

FIG. 3 is a block diagram illustrating the detailed configuration of the radiographic image capture system according to the first exemplary embodiment;

DETAILED DESCRIPTION

First Exemplary Embodiment

FIG. 1 illustrates an example of the schematic configuration of a radiographic image capture system according to the first embodiment. In the first embodiment, similar radiographic image capture system are respectively disposed in X-ray rooms R1 and R2 in order to capture a radiographic (in the first embodiment, X-rays) image.

Each of the radiographic image capture systems that is disposed in each of the X-ray rooms R1 and R2 includes an image capture controller (hereinafter, also referred to as "console") 42, a radiation generator 34, and a radiographic image capture device (hereinafter, also referred to as "electronic cassette" or "cassette") 32. In one room (one radiographic image capture system), one or more electronic cassettes 32 may be provided. Because each of the electronic cassettes 32 is portable, each electronic cassette can be carried from a certain X-ray room to another X-ray room and used in the radiographic image capture system in the other X-ray room.

Figure 2A:
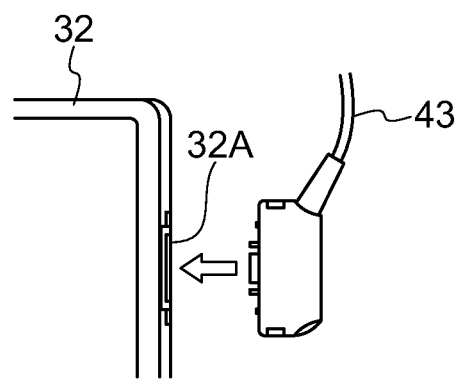
FIG. 2A is a diagram illustrating a state in which a tip end of a cable is connected to a connecting terminal of an electronic cassette.
Figure 2B:
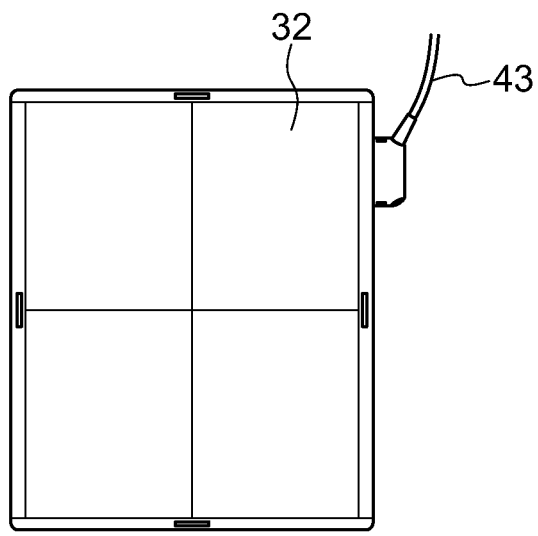
FIG. 2B is a diagram illustrating a state in which the tip end of the cable is connected to the connecting terminal of the electronic cassette.

The console 42 is configured to perform communication with the electronic cassette 32 through a communication base station 20. In the first embodiment, the communication base station 20 for performing wireless communication is provided for each of the X-ray rooms (each of the radiographic image capture systems). The console 42 and the electronic cassette 32 can perform wired communication when wire-connected via a cable 43. As illustrated in FIG. 2, a connecting terminal 32A is provided in the electronic cassette 32. The console 42 and the electronic cassette 32 are wire-connected when one end of the cable 43 is connected to the console 42, and the other end of the cable 43 is connected to the connecting terminal 32A.

The console 42 performs wired or wireless communication, and transmits a control signal in order to perform various control operations with respect to the electronic cassette 32. The console 42 is connected to the radiation generator 34 through a cable 35 and controls the timing when the radiation is generated.

At a timing based on the control of the console 42, the radiation generator 34 applies radiation onto a subject 10. The radiation that is irradiated from the radiation generator 34 transmits through the subject 10 and is irradiated onto the electronic cassette 32. The electronic cassette 32 generates radiographic image information (data) from the irradiated radiation. The generated image data is transmitted to the console 42 using wired or wireless communication.

FIG. 3 is a block diagram illustrating the detailed configuration of the radiographic image capture system according to the first embodiment.

The radiation generator 34 includes a connecting terminal 34A for performing communication with the console 42. The console 42 includes a connecting terminal 42A for performing communication with the radiation generator 34 and a connecting terminal 42B for performing communication with the electronic cassette 32.

The radiation generator 34 is connected to the console 42 through the cable 35. The cable 43 is connected to the connecting terminal 32A of the electronic cassette 32 when a radiographic image is captured and the electronic cassette 32 is connected to the console 42 through the cable 43.

A radiation detector 60 that is incorporated in the electronic cassette 32 is configured with a photoelectric conversion layer that is stacked on a TFT active matrix substrate 66, and is for absorbing radiation X and converting the radiation into charges. The photoelectric conversion layer is made of amorphous a-Se (amorphous selenium) containing selenium as a principal component (for example, having content rate of 50% or more). When radiation X is irradiated, the photoelectric conversion layer internally generates charges (pairs of electron and hole) of a charge amount according to the irradiated radiation dose and converts the irradiated radiation X into the charges. Alternatively, the radiation detector 60 may indirectly convert the irradiated radiation X into charges using a phosphor material and a photoelectric conversion element (photodiode), instead of a radiation-charge conversion material such as the amorphous selenium that directly converts radiation X into charges. As the phosphor material, gadolinium oxysulfide (GOS) or cesium iodide (CsI) can be used. In this case, radiation X is converted into light by the phosphor material and the light is converted into charges by the photodiode of the photoelectric conversion element.

On the TFT active matrix substrate 66, plural pixels 74 (in FIG. 3, the photoelectric conversion layer corresponding to each pixel 74 is schematically illustrated as a photoelectric conversion unit 72) each of which includes a storage capacitor 68 that accumulates charges generated by the photoelectric conversion layer and a TFT 70 that reads the charges accumulated in the storage capacitor 68 are arranged in a matrix. The charges that are generated in the photoelectric conversion layer due to irradiation of radiation X onto the electronic cassette 32 are accumulated in the storage capacitor 68 of each of the pixels 74. Thereby, image information that has been carried in the radiation X irradiated onto the electronic cassette 32 is converted into charge information and is held in the radiation detector 60.

The TFT active matrix substrate 66 includes plural gate lines 76 that extend in one direction (row direction) and are used to turn on/off the TFT 70 of each pixel 74, and plural data lines 78 that extend in a direction (column direction) substantially orthogonal to the gate lines 76 and are used to read the accumulated charges from the storage capacitor 68 through a TFT 70 which has been turned on. Each gate line 76 is connected to a gate line driver 80 and each data line 78 is connected to a signal processor 82. When charges are accumulated in the storage capacitor 68 of each pixel 74, the TFT 70 of each pixel 74 is sequentially turned on in a row unit by a signal supplied from the gate line driver 80 through the gate line 76. The charges are accumulated in the storage capacitor 68 of the pixel 74 where the TFT 70 is turned on are transmitted as an analog electric signal through the data line 78 and are input to the signal processor 82. Accordingly, the charges are accumulated in the storage capacitor 68 of each pixel 74 are sequentially read in a row unit.

Although not illustrated in the drawings, the signal processor 82 includes an amplifier and a sampling/holding circuit that are provided for each data line 78. The charge signal that is transmitted through each data line 78 is amplified by the amplifier and is held in the sampling/holding circuit. A multiplexer and an analog/digital (A/D) converter are sequentially connected to the output end of the sampling/holding circuit, and the charge signal that is held in each sampling/holding circuit is sequentially (serially) input to the multiplexer and is converted into digital image data by the A/D converter.

An image memory 90 is connected to the signal processor 82, and the image data that is output from the A/D converter of the signal processor 82 is sequentially stored in the image memory 90. The image memory 90 has a storage capacity that can store image data indicating a predetermined number of frames' worth of radiographic images, and each time the charges are read line by line, image data corresponding to each read line is sequentially stored in the image memory 90.

The image memory 90 is connected to a cassette controller 92 that controls the entire operation of the electronic cassette 32. The cassette controller 92 is realized by a microcomputer and includes a CPU 92A, memory 92B including ROM and RAM, and a non-volatile storage unit 92C including an HDD or flash memory.

A wireless communication unit 94 and a wired communication unit 95 are connected to the cassette controller 92. The wireless communication unit 94 complies with a wireless local area network (LAN) standard that typically includes the Institute of Electrical and Electronics Engineers (IEEE) 802.11a/b/g, and controls transmission of various data between external devices and the wireless communication unit 94 using wireless communication. The wired communication unit 95 complies with a wired LAN standard, is connected to the connecting terminal 32A, and controls transmission of various data between the console 42 and the wired communication unit through the connecting terminal 32A and the cable 43. The cassette controller 92 performs transmission and reception of various data between the console 42 and the cassette controller 92 through the wireless communication unit 94 or the wired communication unit 95.

The cassette controller 92 is connected to a detection unit 33. The detection unit 33 is connected to the connecting terminal 32A and detects whether the console 42 is connected to the connecting terminal 32A through the cable 43.

In a case in which the connecting terminal 32A is a connector configured with plural pins, any of the plural pins can be used as a pin used for connection detection and a connection state can be detected by measuring a voltage of the corresponding pin. For example, in a case in which each of the connecting terminal 42A of the console 42 and the connecting terminal 32A of the electronic cassette 32 is a connector configured with ten pins, the first and tenth pins among the ten pins can be used as pins for connection detection. The first and tenth pins of the connecting terminal 42A of the console 42 are short-circuited, the first pin of the connecting terminal 32A of the electronic cassette 32 is grounded (set to 0 V), and the tenth pin of the connecting terminal 32A is pulled up to a predetermined voltage.

In this state, when one end of the cable 43 is connected to the connecting terminal 42A of the console 42 and the other end thereof is connected to the connecting terminal 32A of the electronic cassette 32 and thereby the console 42 is wire-connected to the connecting terminal 32A of the electronic cassette 32e, the voltage of the tenth pin of the connecting terminal 32A is detected as 0 V by the detection unit 33 (because the pins are short-circuited in the console 42).

Further, when the console 42 is disconnected from the connecting terminal 32A (including three cases of: when one end of the cable 43 is disconnected from the connecting terminal 42A of the console 42, when the other end of the cable 43 is disconnected from the connecting terminal 32A of the electronic cassette 32, and when both ends of the cable 43 are disconnected from the connecting terminals 32A and 42A), because the tenth pin of the connecting terminal 32A is pulled up, the pulled-up voltage is detected by the detection unit 33.

In this way, the detection unit 33 can detect the voltage of the pin for connection detection in the connecting terminal 32A and output a detection signal indicating the detected voltage to the cassette controller 92. The cassette controller 92 can recognize whether or not the console 42 is wire-connected to the connecting terminal 32A, using the detection signals.

The method of detecting the wired connection is not limited to the above method. For example, in the LAN specification specifies a signal that is called a link signal, and when a connection is established, the link signal becomes active. Therefore, whether or not the console 42 is connected to the connecting terminal 32A can be detected also by detecting a state of the link signal by a driver of the LAN. Further alternatively, for example, the connecting terminal 32A may be provided with a switch that is turned on when the tip end of the cable 43 is fitted into the connecting terminal 32A and is turned off when the cable 43 is disconnected from the connecting terminal 32A, and a connecting state may be easily detected by detecting a state of the switch. In the case in which this detection method is adopted, one end of the cable 43 always needs to be connected to the connecting terminal 42A of the console 42.

A power supply unit 96 is provided in the electronic cassette 32 and various circuits or elements (the detection unit 33, the gate line driver 80, the signal processor 82, the image memory 90, the wireless communication unit 94, the wired communication unit 95, and the microcomputer functioning as the cassette controller 92) described above operates by power supplied from the power supply unit 96. The power supply unit 96 is charged by power that is supplied through the cable 43 when the cable 43 is connected to the connecting terminal 32A. The power supply unit 96 incorporates a battery (chargeable secondary battery) so that the portability of the electronic cassette 32 is not deteriorated, and supplies power from the charged battery to the various circuits and elements. Although a secondary battery is used as the battery in the present embodiment, embodiments are not limited thereto and the battery may be a primary battery. In FIG. 3, wirings that connect the power supply unit 96 and the various circuits and elements are not illustrated.

The console 42 is configured as a server computer and includes a display 100 that displays an operation menu or a captured radiographic image, and an operation panel 102 that includes plural keys and receives various data or operation instructions.

The console 42 according to the first embodiment includes a CPU 104 that controls an entire operation of the device, a ROM 106 in which various programs including a control program are stored in advance, a RAM 108 that temporarily stores various data, an HDD 110 that stores and maintains various data, a display driver 112 that controls display of various data with respect to the display 100, an operation input detector 114 that detects an operation state with respect to the operation panel 102, a communication interface (UF) unit 116 that is connected to the connecting terminal 42A and transmits and receives various data such as exposure conditions to be described below between the radiation generator 34 and the communication UF unit through the connecting terminal 42A and the cable 35, a wireless communication unit 118 that transmits and receives various data between the electronic cassette 32 and the wireless communication unit by the wireless communication, and a wired communication unit 120 that is connected to the connecting terminal 42B and transmits and receives various data between the electronic cassette 32 and the wired communication unit through the connecting terminal 42B and the cable 43.

The CPU 104, the ROM 106, the RAM 108, the HDD 110, the display driver 112, the operation input detector 114, the communication I/F unit 116, the wireless communication unit 118, and the wired communication unit 120 are connected to each other through a system bus BUS. Therefore, the CPU 104 can access to the ROM 106, the RAM 108, and the HDD 110, and can perform control of displaying various data with respect to the display 100 by the display driver 112, control of transmission/reception of various data with the radiation generator 34 by the communication I/F unit 116, control of transmission/reception of various data with the electronic cassette 32 by the wireless communication unit 118, and control of transmission/reception of various data with the electronic cassette 32 by the wired communication unit 120. Further, the CPU 104 can grasp an operation state of a user with respect to the operation panel 102 using the operation input detector 114.

The radiation generator 34 includes a radiation source 130 that outputs radiation X, a communication OF unit 132 that transmits and receives various data such as exposure conditions between the console 42 and the communication OF unit, and a radiation source controller 134 that controls the radiation source 130 on the basis of the received exposure conditions.

The radiation source controller 134 is realized by a microcomputer, and stores the received exposure conditions. The exposure conditions received from the console 42 includes data of a tube voltage, a tube current, an irradiation period and the like. The radiation source controller 134 irradiates the radiation X from the radiation source 130 on the basis of the received exposure conditions.

Next, an operation of the radiographic image capture system according to the first embodiment will be described.

The communication base station 20 that is an access point used in each X-ray room holds extended service set identifier (ESSID) and a channel Ch as wireless communication configuration data used to perform wireless communication. Each console 42 used in each X-ray room holds the same ESSID and channel Ch as those set in the communication base station 20 of the X-ray room where the console 42 is disposed. The ESSID and the channel Ch are set in advance by being stored in the HDD 110 or the ROM 106 of the console 42. Further, the same ESSID and channel Ch are also set in the electronic cassette 32 that is used in the same radiographic image capture system, by being stored in advance in the storage unit 92C of the electronic cassette 32.

In this case, only one ESSID and only one channel Ch are set to the console 42 and the electronic cassette 32, and plural ESSIDs will never be set to each of the devices.

The communication base station 20 to which the electronic cassette 32 and the console 42 are connected when wireless communication is performed is respectively identified by the ESSID. That is, only the devices which have been set the same set ESSID can perform communication with each other. The wireless communication unit 94 of the electronic cassette 32 performs wireless communication after confirming and authenticating that the ESSIDs of the communication base station 20 and the electronic cassette 32 matches. The wireless communication unit 118 of the console 42 also performs similar conformation and authentication before performing communication.

Further, in, a frequency band to be used in wireless communication is divided such that plural devices can simultaneously perform communications. The channel Ch indicates these divided frequency bands. In the first embodiment, different channels for devices in different X-ray rooms are assigned to in order to prevent interference of the electric waves between the communication base stations 20. Therefore, the wireless communication unit 94 of the electronic cassette 32 and the wireless communication unit 118 of the console 42 perform wireless communication at the frequency band according to the set channel Ch when performing wireless communication.

Each of the electronic cassette 32 and the console 42 holds in advance a unique address (in the first embodiment, an IP address, specifically, a local IP address) to identify itself. Specifically, the unique address may be held in the storage unit 92C in the electronic cassette 32, and may be held in the HDD 110 in the console 42. In the first embodiment, the held IP address includes a local IP address for wired communication and a local IP address for wireless communication. Hereinafter, the local IP address for the wired communication is called a wired IP address, and the local IP address for the wireless communication is called a wireless IP address. When communication is performed, an IP address read according to whether the communication mode is wired or wireless system and is used.

Figure 4:
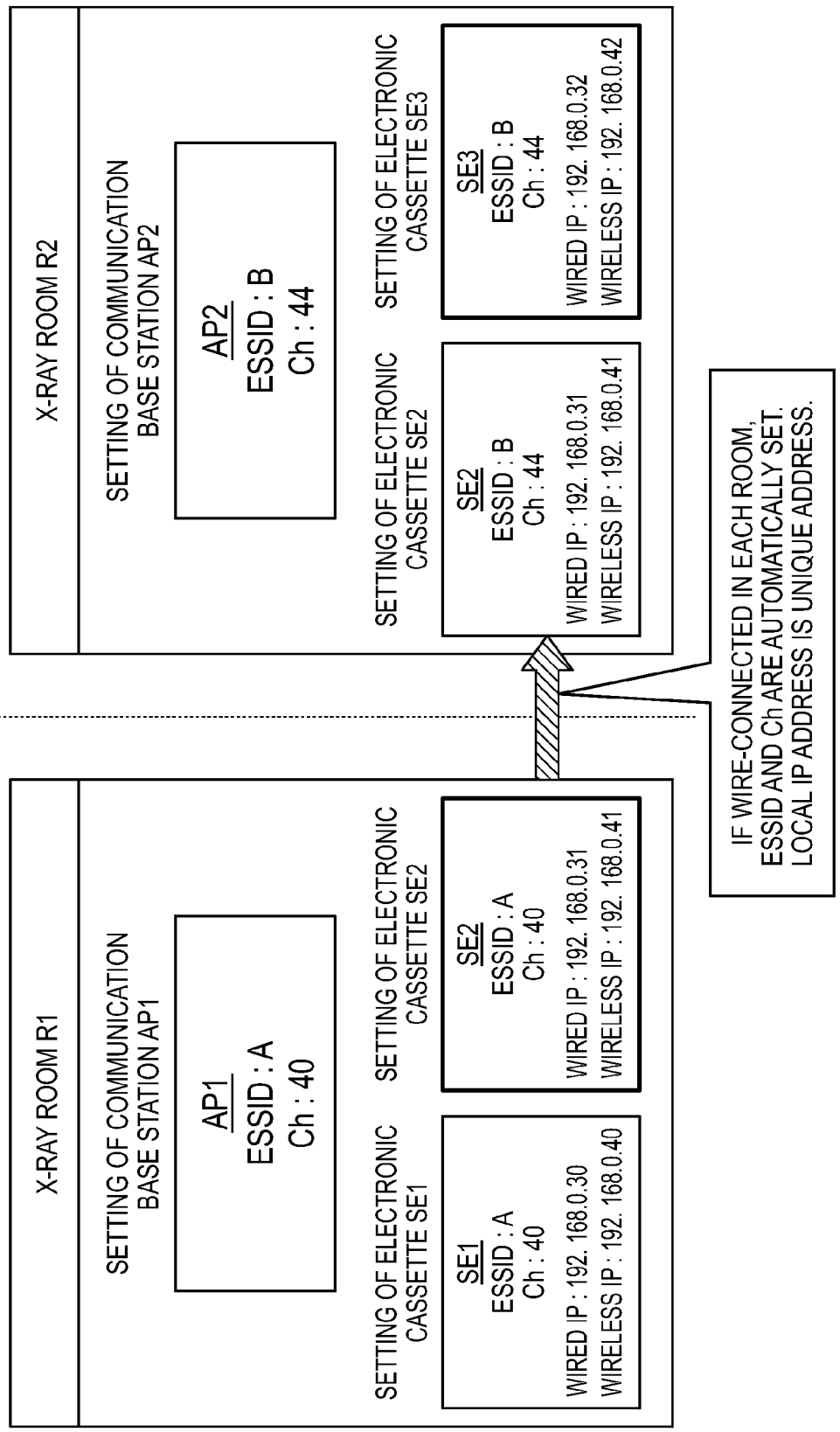
FIG. 4 is a diagram illustrating setting (configuration) contents of communication information (data) of communication base stations and the electronic cassettes in X-ray rooms.

FIG. 4 illustrates an example of setting contents of the communication data. The communication base station 20 (in FIG. 4, communication base station AP1) that is the access point used in the X-ray room R1 is set with wireless communication configuration data indicating ESSID "A" and channel Ch "40". Two electronic cassettes 32 (in FIG. 4, electronic cassettes SE1 and SE2) that are originally included in the radiographic image capture system of the X-ray room R1 are set with the same ESSID "A" and channel Ch "40" as those of the communication base station AP1. The electronic cassettes SE1 and SE2 are also given with the wired IP addresses and the wireless IP addresses that are respectively different from each other. Although not illustrated in FIG. 4, the console 42 disposed in the X-ray room R1 is also set with ESSID "A", channel Ch "40", and the wired IP address and the wireless IP address for identifying the console 42.

The communication base station 20 (hereinafter, referred to as communication base station AP2) that is the access point used in the X-ray room R2 is set with wireless communication configuration data indicating ESSID "B" and channel Ch "44". The electronic cassette 32 (in FIG. 4, electronic cassette SE3) that is originally included in the radiographic image capture system of the X-ray room R2 is set with the same ESSID "B" and channel Ch "44" as those of the communication base station AP2. The electronic cassette SE3 is also set with wired IP address and wireless IP address which are mutually different. Although not illustrated in FIG. 4, the console 42 disposed in the X-ray room R2 is also set with ESSID "B", channel Ch "44", and the wired IP address and the wireless IP address for identifying the console 42.

Here, a case in which the electronic cassette SE2 in the radiographic image capture system of the X-ray room R1 is moved to the X-ray room R2 and is used in the radiographic image capture system of the X-ray room R2 is considered. In this case, because the ESSIDs and the channels Ch in the wireless communication configuration data are respectively different in the X-ray rooms R1 and R2, when the electronic cassette SE2 performs wireless communication after the electronic cassette SE2 is moved to the X-ray room R2, (if the electronic cassette SE2 is in an area in which electric waves from the X-ray room R1 reach), the electronic cassette SE2 performs wireless communication with the communication base station AP1 of the X-ray room R1 and cannot perform wireless communication with the communication base station AP2 of the X-ray room R2.

Therefore, in the first embodiment, as illustrated in FIG. 4, the wireless communication configuration data of the electronic cassette SE2 is updated (rewritten), such that wireless communication with the communication base station AP2 of the X-ray room R2 can be performed. Hereinafter, the update operation will be described in detail. Because the same operation is performed with respect to all of the electronic cassettes 32 including the electronic cassette SE2 when the electronic cassettes are moved between the X-ray rooms and are used, the following operation is described as an operation of each electronic cassette 32.

In a case in which the user moves the electronic cassette 32 from one X-ray room to the other X-ray room, the user wire-connects the electronic cassette 32 to the console 42 of the other X-ray room. That is, the user wire-connects the connecting terminal 32A of the electronic cassette 32 to the console 42 by connecting one end of the cable 43 to the connecting terminal 32A of the electronic cassette 32 and connecting the other end thereof to the connecting terminal 42A of the console 42 of the X-ray room that the electronic cassette 32 has been moved.

Figure 5A:
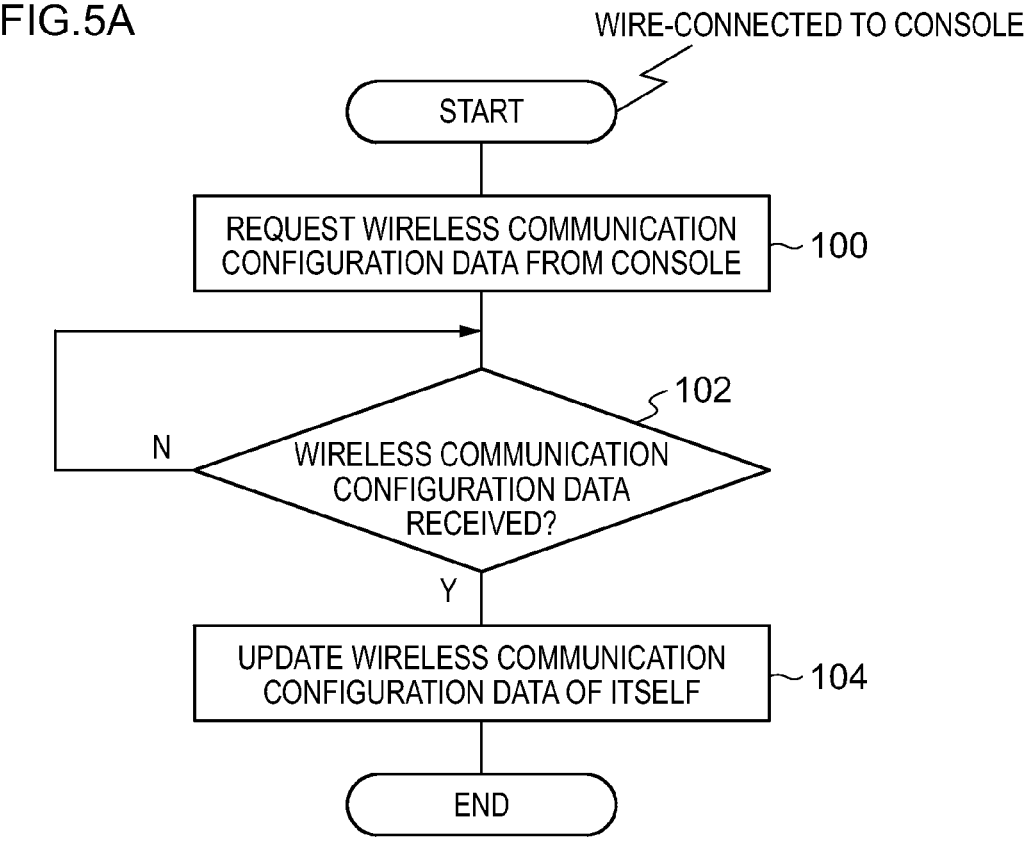
FIG. 5A is a flowchart illustrating a flow of a program that is executed by a CPU of the electronic cassette.

FIG. 5A is a flowchart illustrating a process of a wireless communication configuration program that is executed by the CPU 92A of the electronic cassette 32. The wireless communication configuration program is stored in advance in a predetermined area of the memory 92B (ROM).

In a case in which the detection unit 33 detects that the console 42 and the electronic cassette 32 are wire-connected by the wire, the process that is illustrated in FIG. 5A is executed. In step 100, the electronic cassette 32 requests the console 42 connected by the wire to transmit the wireless communication configuration data (in the first embodiment, the ESSID and the channel Ch) set in the console 42 using the wired communication. In step 102, the electronic cassette 32 waits for reception of the wireless communication configuration data. If the wireless communication configuration data is received from the console 42 connected by the wire through the wired communication, the determination in step 102 is affirmative (YES) and the process proceeds to step 104. In step 104, the electronic cassette 32 updates the wireless communication configuration data that is stored and set in itself, with the received wireless communication configuration data. That is, the electronic cassette 32 rewrites the wireless communication configuration data stored in the self device with the wireless communication configuration data received from the console 42 that is wire-connected.

Figure 5B:
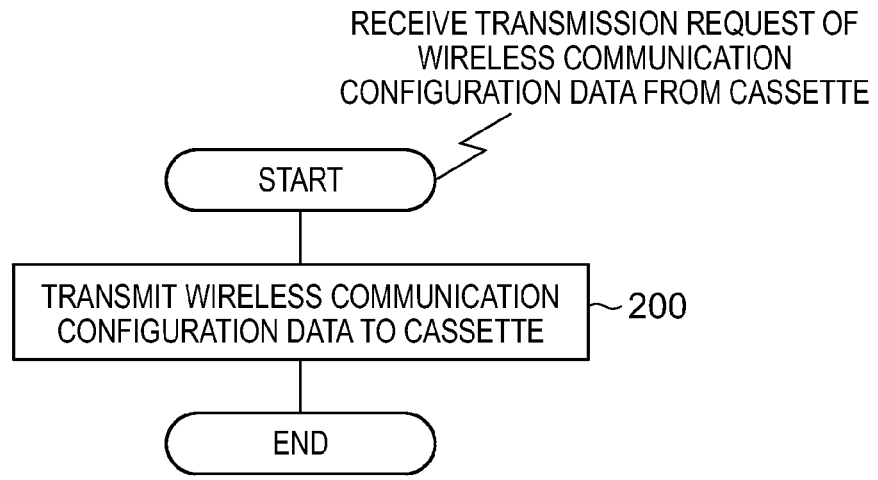
FIG. 5B is a flowchart illustrating a flow of a program that is executed by a CPU of a console.

Meanwhile, the console 42 executes the process that is illustrated in FIG. 5B. FIG. 5B is a flowchart illustrating a process of a wireless communication configuration data transmission program that is executed by the CPU 104 of the console 42. The wireless communication configuration data transmission program is stored in advance in the predetermined area of the memory 106 (ROM) or the HDD 110. In a case in which the transmission request of the wireless communication configuration data is received from the electronic cassette 32 that is wire-connected, in step 200, the console 42 reads the wireless communication configuration data that is set to itself and transmits the wireless communication configuration data to the electronic cassette 32 that is the requester via wired communication. Thus, the determination in step 102 of FIG. 5A is affirmative.

As described above, the electronic cassette 32 is configured such that, in a case in which the electronic cassette 32 is wire-connected to the console 42, the electronic cassette 32 acquires the wireless communication configuration data from the console 42 that is wire-connected and updates the wireless communication configuration data of itself. Therefore, the wireless communication configuration data of the electronic cassette 32 can be updated without a user intervening.

Accordingly, the electronic cassette 32 can perform wireless communication with respect to the communication base station 20 in the movement destination, and a situation such that an image being captured in a site that the electronic cassette 32 was originally placed can be prevented.

In the first embodiment, the detection unit 33 continuously monitors the wired connection state with the console 42, and updates the wireless communication configuration data when wired connection is detected. However, embodiments are not limited thereto. For example, the wired connection state may be checked at a predetermined time interval and the wireless communication configuration data of the electronic cassette 32 may be updated at that time. The wired connection state may also be detected at a predetermined timing (for example, when initiation of the entire system or at the time when power supply is turned on in the electronic cassette 32) and the wireless communication configuration data may be updated at that time.

Second Exemplary Embodiment

In the first embodiment, the electronic cassette 32 detects by the detection unit 33 the wired connection state with the console 42, requests transmission of the wireless communication configuration data from the console 42, and acquires and updates the wireless communication configuration data of itself. However, embodiments are not limited thereto, and the console 42 may detect the wired connection state with the electronic cassette 32 and transmit the wireless communication configuration data of itself to the electronic cassette 32 in order to update the wireless communication configuration data of the electronic cassette 32.

Figure 6:
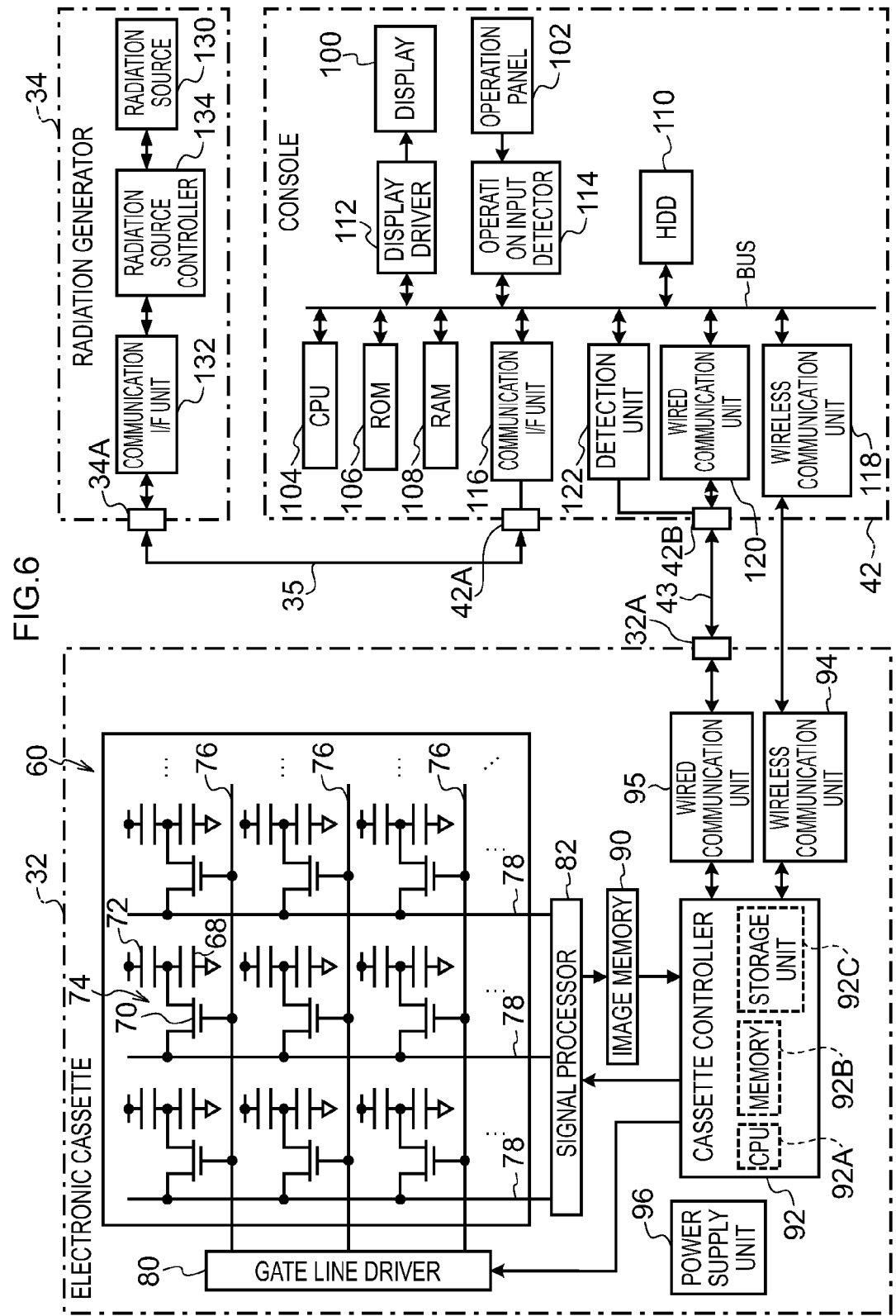
FIG. 6 is a block diagram illustrating the detailed configuration of the radiographic image capture system according to the second exemplary embodiment.

FIG. 6 is a block diagram illustrating the detailed configuration of a radiographic image capture system according to the second embodiment. In FIG. 6, components denoted by same reference numerals as those in FIG. 3 have same functions as the corresponding components of FIG. 3 and, therefore, duplicated description is omitted.

As illustrated in FIG. 6, in the second embodiment, instead of providing the detection unit 33 in the electronic cassette 32, a detection unit 122 is provided in the console 42. The detection unit 122 of the console 42 is connected to the connecting terminal 42A and detects whether or not the electronic cassette 32 is wire-connected to the connecting terminal 42A through the cable 43 (that is, the detection unit 122 detects wired connection state of the console 42 with the electronic cassette 32). The detection result is transmitted to the CPU 104 through the system bus BUS. Since the detection unit can use the same detecting method as that of the detection unit 33 of the electronic cassette 32 described in the first embodiment, detail description thereof is not repeated.

Next, an operation of the radiographic image capture system according to the second embodiment will be described.

Figure 7:
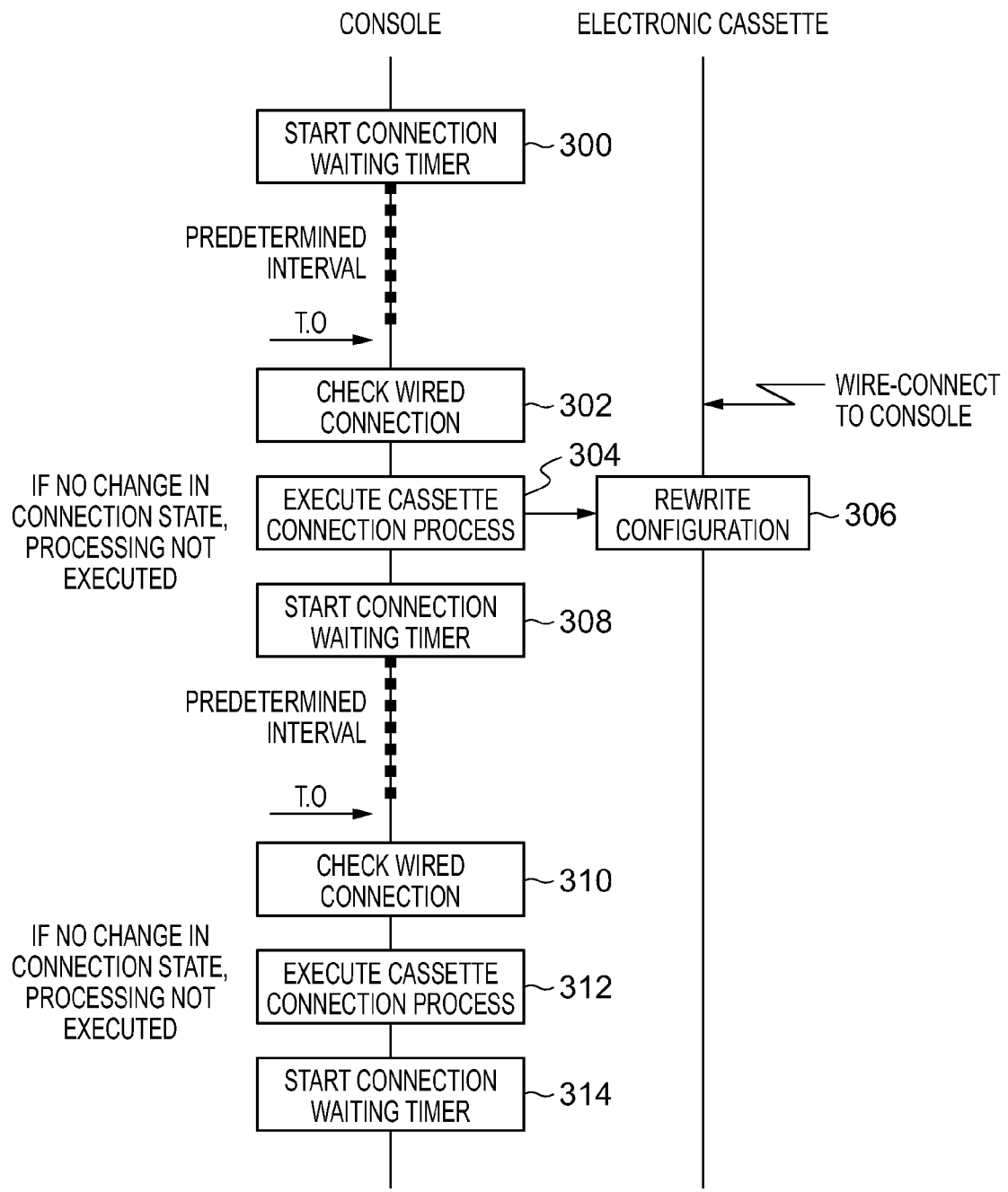
FIG. 7 is a timing chart illustrating an operation of the radiographic image capture system according to the second exemplary embodiment.

FIG. 7 illustrates a timing chart of the operation of the radiographic image capture system according to the second embodiment. First, the console 42 resets a connection waiting timer and starts clocking (step 300). In the second embodiment, the console 42 confirms whether the electronic cassette 32 is wire-connected to the connecting terminal 42A, at a predetermined time interval. The waiting is a timer is for measuring the predetermined time interval, which is not illustrated in FIG. 7. In this case, the connection waiting timer is a counting-down timer.

When a predetermined time elapses after the clocking of the connection waiting timer starts, the connection waiting timer times out. At this time, the console 42 checks whether or not the electronic cassette 32 is wire-connected, using the detection unit 122 (step 302). If it is confirmed that the electronic cassette 32 is wire-connected, the console 42 executes a cassette connection process (step 304). The cassette connection process is a process of transmitting a control signal including the wireless communication configuration data of itself to the electronic cassette 32 that is wire-connected using the wired communication, and updating the configuration of the electronic cassette 32. In response, the electronic cassette 32 rewrites by the cassette controller 92 the communication configuration according to the control signal (step 306).

In the second embodiment, in a case in which there is no change in the connection state between the current checking time and the previous checking time (the checking time immediately before the current checking time), i.e., in a case in which a wired connection state with the same electronic cassette 32 is detected at both the current checking time and previous checking time, the console 42 does not execute the cassette connection process. This determination can be made, for example, by checking whether or not the wired IP address of the electronic cassette 32 that is wire-connected is the same at the current checking time as at the previous checking time. Of course, in a case in which the electronic cassette 32 is not wire-connected, the console does not execute the cassette connection process.

Then, the console 42 resets the connection waiting timer and re-starts the clocking (step 308). When the predetermined time elapses after the clocking of the connection waiting timer starts, the connection waiting timer times out. At this time, the console 42 checks whether or not the electronic cassette 32 is wire-connected, using the detection unit 122 (step 310). After the checking, in a case in which it is detected that the electronic cassette 32 having a different wired IP address from that of the electronic cassette 32 at the time of previous checking is wire-connected, the console 42 executes the cassette connection process (step 312). However, as illustrated in FIG. 7, in a case in which there is no change in the connection state between the previous checking time and the current checking time, the console 42 does not execute the cassette connection process. Next, the console 42 resets the connection waiting timer and re-starts the clocking (step 314). The same process as described above is repeated.

In the above description, a case is explained in which in step 302, the wired connection state is determined only based on the detection result of the detection unit 122. However, embodiments are not limited thereto, and the wired connection state may be determined based on the detection result of the detection unit 122 and a response result from the electronic cassette 32 as a result of transmitting, via wired communication, a predetermined signal for checking whether or not actual wired communication can be performed.

Figure 8:
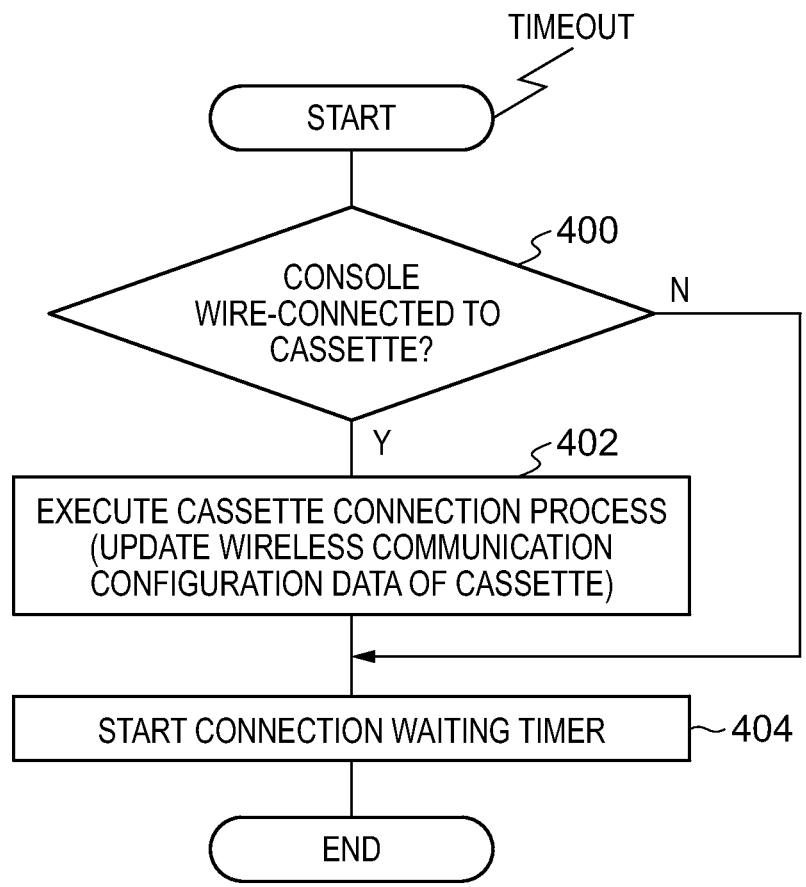
FIG. 8 is a flowchart illustrating a flow of a program that is executed by a CPU of a console according to the second exemplary embodiment.

The operation of the second embodiment will be now described by focusing on the process of the console 42 illustrated in the timing chart. FIG. 8 is a flowchart illustrating a process of an update program that is executed by the CPU 104 of the console 42. The update program is stored in advance in a predetermined area of the memory 106 (ROM) or the HDD 110.

After the connection waiting timer times out, the process that is illustrated in FIG. 8 is executed. In step 400, the console 42 determines whether or not the console 42 is wire-connected to the electronic cassette 32, based on the detection signal from the detection unit 122. If the determination result is affirmative, the cassette connection process is executed in step 402. However, as described above, if there is no change in the connection state from the previous determination, the console 42 does not execute the cassette connection process (not illustrated). In step 404, the console 42 resets the connection waiting timer, re-starts the clocking, and terminates the process.

In the present embodiment, a case in which the console 42 detects the connection state with the electronic cassette 32 at the predetermined time interval and executes the cassette connection process is described. However, embodiments are not limited thereto. For example, the console 42 may continuously monitor the detection signal of the detection unit 122, and execute the cassette connection process when the detection signal of the detection unit 122 changes (that is, when the connection state of the electronic cassette 32 changes from a state in which the electronic cassette 32 is not wire-connected to a state in which the electronic cassette 32 is wire-connected). The wired connection state may be detected and the wireless communication configuration data may be updated, at predetermined timing (for example, when the entire system starts).

As described above, in the present embodiment, since the electronic cassette 32 is configured to transmit, when the electronic cassette 32 is wire-connected to the console 42, the wireless communication configuration data set to itself to the electronic cassette 32 to which the console 42 is wire-connected and causes the electronic cassette 32 to update the wireless communication configuration data, the same effect as that of the first embodiment can be obtained.

Figure 9A:
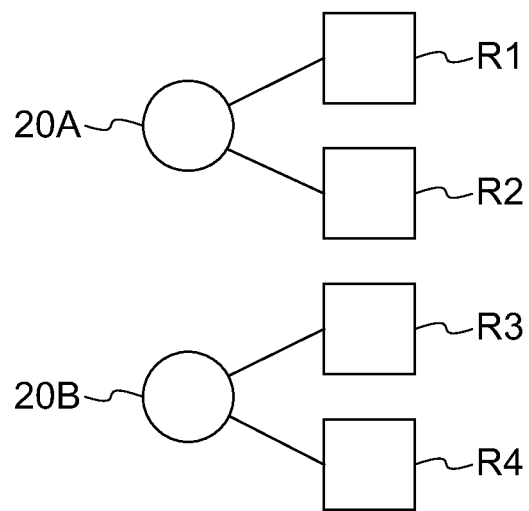
FIG. 9A is a diagram illustrating a case in which the number of the X-ray rooms to be associated with each of the communication base stations is equalized.

In the first and second embodiments, cases in which one radiographic image capture system is disposed in each of the rooms (X-ray rooms) and one communication base station 20 is provided in each of the rooms (X-ray rooms). However, embodiments are not limited thereto and, as illustrated in FIG. 9A, one communication base station 20 may be provided for two or more rooms. In FIG. 9A, four X-ray rooms R1, R2, R3, and R4 are provided, the communication base station 20A is provided for the X-ray rooms R1 and R2, and the communication base station 20B is provided for the X-ray rooms R3 and R4. Since the number of rooms associated to each of the communication base stations 20A and 20B is equal, the communication load is equalized between the communication base stations 20A and 20B. Specifically, the radiographic image capture system in each of the X-ray rooms R1 and R2 performs communication using the communication base station 20A, and the radiographic image capture system in each of the X-ray rooms R3 and R4 performs communication using the communication base station 20B. In this case, since the two or more image capture operations will not be performed in parallel in one X-ray room, the communication base stations 20A and 20B are used for image captures in the respective two rooms. Even if the electronic cassette 32 is moved between the rooms, the wireless communication configuration data of the moved electronic cassette 32 is updated as described above. Therefore, a situation can be prevented such that X-ray irradiation is erroneously instructed to the moved electronic cassette 32 in the X-ray room from which the electronic cassette 32 has been moved.

Figure 9B:
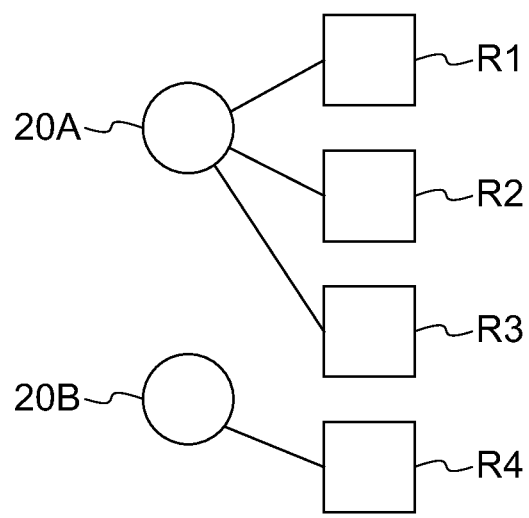
FIG. 9B is a diagram illustrating a case in which the number of the X-ray rooms to be associated with each of the communication base stations are different.

If, as illustrated in FIG. 9B, a different number of X-ray rooms is associated to each of the communication base stations 20, such that the communication base station 20A is provided for the X-ray rooms R1, R2, and R3, and the communication base station 20B is provided for the X-ray room R4, it is difficult to equalize the communication load between the communication base stations 20A and 20B. Accordingly, it is preferable to configure such that the number of X-ray rooms associated to each of the communication base stations 20 is equalized.

Examples of the combination of the communication base station and the X-ray rooms are not limited to the example illustrated in FIG. 9A. For example, one communication base station 20 may be associated to every three rooms, or one communication base station 20 may be associated to every four rooms. Thus, the communication load can be equalized by distributing the communication load by the combination of the X-ray rooms and the communication base stations 20.

In the first and second embodiments, the console 42 and the radiation generator 34 are provided as the separate devices. However, embodiments are not limited thereto. For example, the console 42 and the radiation generator 34 may be configured as a single device.

In the first and second embodiments, X-ray is applied as radiation. However, embodiments are not limited thereto and gamma rays or the like may be applied as radiation.

The specific configuration of the radiographic image capture system (shown in FIGS. 1, 3, and 6) and the shape of the cable (shown in FIG. 2) described in the first and second embodiments are examples and the configuration and the shape may be changed depending on the situation of application within a range that does not depart from the gist of the invention.

Further, the processes described in the first and second embodiments (FIGS. 5, 7, and 8) are examples and the processes may be changed depending on the situation of application within a range that does not depart from the gist of the invention.

What is claimed is:

1. A portable radiographic image capture device that is carried between locations of a plurality of image capture controllers, wherein a communication base station for wireless communication is pre-specified for each of the plurality of image capture controllers, the portable radiographic image capture device comprising:
    an image data generating unit that generates radiographic image data from irradiated radiation;
    a wired communication unit that comprises a connecting terminal, and performs wired communication with an image capture controller that is wire-connected to the connecting terminal;
    a wireless communication unit that performs wireless communication with a communication base station;
    a storing unit that stores first wireless communication configuration data related to a first communication base station with which the wireless communication unit performs wireless communication;
    a detection unit that detects that an image capture controller of a carried location is wire-connected to the connecting terminal; and
    an update unit that, when the detection unit detects that the image capture controller of the carried location is wire-connected to the connecting terminal, acquires from the image capture controller second wireless communication configuration data related to a second communication base station which is pre-specified for the image capture controller to perform wireless communication, and updates the first wireless communication configuration data held in the storing unit with the acquired second wireless communication configuration data.

2. The portable radiographic image capture device according to claim 1, wherein the first and second wireless communication configuration data includes data that identifies a communication base station to be connected when wireless communication is performed.

3. A radiographic image capture system, comprising:
    the portable radiographic image capture device according to claim 1, wherein the update unit acquires the second wireless communication configuration data by making a request to an image capture controller; and an image capture controller that comprises:
- a second wired communication unit that performs wired communication with the portable radiographic image capture device that is wire-connected thereto;
- a second wireless communication unit that performs wireless communication with the second communication base station; and
- a controlling unit that effects control such that, when the image capture controller is wire-connected to the connecting terminal of the portable radiographic image capture device and receives the request from the portable radiographic image capture device, the second wireless communication configuration data related to the second communication base station is transmitted to the portable radiographic image capture device.

4. The radiographic image capture system according to claim 3, wherein the first and second wireless communication configuration data includes data that identifies a communication base station to be connected when wireless communication is performed.

5. The portable radiographic image capture device according to claim 1, wherein the update unit updates the first wireless communication configuration data held in the storing unit with the acquired second wireless communication configuration data every time the detection unit detects that an image capture controller is wire-connected to the connecting terminal.

6. An image capture controller, comprising:
- a connecting terminal that is used to perform wired connection with a portable radiographic image capture device, which includes an image data generating unit that generates radiographic image data from irradiated radiation, a first wired communication unit that performs wired communication with the image capture controller when wire-connected thereto, a first wireless communication unit that performs wireless communication with a communication base station, a storing unit that stores first wireless communication configuration data related to a first communication base station with which the first wireless communication unit performs wireless communication, and an update unit that updates the wireless communication configuration data held in the holding unit;
- a second wired communication unit that performs wired communication with the portable radiographic image capture device wire-connected to the connecting terminal;
- a second wireless communication unit that performs wireless communication with a second communication base station; and
- a controlling unit that effects control such that, when the portable radiographic image capture device is wire-connected to the connecting terminal, second wireless communication configuration data related to the second communication base station is transmitted to the portable radiographic image capture device, and the update unit updates the first wireless communication configuration data stored in the storing unit with the second wireless communication configuration data.

7. The image capture controller according to claim 6, wherein the wireless communication configuration data includes data that identifies a communication base station to be connected when wireless communication is performed.

8. A radiographic image capture system, comprising:
- a portable radiographic image capture device comprising:
  - an image data generating unit that generates radiographic image data from irradiated radiation;
  - a first wired communication unit that performs wired communication with an image capture controller that is wire-connected;
  - a first wireless communication unit that performs wireless communication with a first communication base station;
  - a storing unit that stores first wireless communication configuration data related to the first communication base station; and
  - an update unit that updates the first wireless communication configuration data stored in the storage unit; and the image capture controller according to claim 6.

9. The radiographic image capture system according to claim 8, wherein the first and second wireless communication configuration data includes data that identifies a communication base station to be connected when wireless communication is performed.

* * * * *